US008693625B2

(12) United States Patent
Dugas et al.

(10) Patent No.: US 8,693,625 B2
(45) Date of Patent: Apr. 8, 2014

(54) DYNAMIC SHAPING TIME MODIFICATION IN X-RAY DETECTORS

(75) Inventors: Michael E. Dugas, Londonderry, NH (US); Lee Grodzins, Lexington, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 232 days.

(21) Appl. No.: 13/127,595

(22) PCT Filed: Nov. 4, 2009

(86) PCT No.: PCT/US2009/063311
§ 371 (c)(1),
(2), (4) Date: May 4, 2011

(87) PCT Pub. No.: WO2010/054018
PCT Pub. Date: May 14, 2010

(65) Prior Publication Data
US 2011/0211670 A1     Sep. 1, 2011

Related U.S. Application Data

(60) Provisional application No. 61/111,252, filed on Nov. 4, 2008.

(51) Int. Cl.
*G01N 23/223*     (2006.01)

(52) U.S. Cl.
USPC ............................................. 378/45; 378/44

(58) Field of Classification Search
USPC .................................................... 378/44, 45
See application file for complete search history.

(56) References Cited

U.S. PATENT DOCUMENTS 7,330,527 B2     2/2008   Hoffman et al.
7,388,534 B2     6/2008   Astley
7,899,153 B2     3/2011   Dugas et al.
8,027,811 B2     9/2011   Camus et al.
2002/0071519 A1*  6/2002  Satoh ............................. 378/49
2006/0029182 A1   2/2006  Tani et al.
2008/0192897 A1   8/2008  Piorek
2008/0319714 A1   12/2008 Camus et al.

FOREIGN PATENT DOCUMENTS

JP     63-103955      5/1988
JP     2008-153256    7/2008

OTHER PUBLICATIONS

T. R. Twomey et al., "High-Count-Rate Spectroscopy with Ge Detectors: Quantitative Evaluation of the Performance of High-Rate Systems," ORTEC Technical Papers (1991), pp. 1-11, http://www.ortec-online.com/pdf/herpaper.pdf.

L. Strueder et al., "High-Resolution X-ray Spectroscopy Close to Room Temperature," Microsc. Microanal. 4 (1999), pp. 622-631.

(Continued)

*Primary Examiner* — Courtney Thomas
(74) *Attorney, Agent, or Firm* — Gordon Stewart

(57) ABSTRACT

Methods and apparatus for adapting the shaping time and/or other pulse processing parameters of an x-ray detector (114) in accordance with the elemental composition of a sample and/or energy resolving requirements. X-rays (104) are directed from a source (102) onto a sample (110) and the radiation (108) responsively emitted from the sample (e.g., fluoresced radiation characteristic of the sample's elemental composition) and detected by an x-ray detector (114) that generates pulses representative of the energy and intensity of the incident radiation. Based upon initial analysis of elemental composition, the shaping time and/or other pulse processing parameter (s) are set to optimize count rate subject to constraints of energy resolution in a spectral region of interest.

6 Claims, 5 Drawing Sheets

(56) References Cited

OTHER PUBLICATIONS

L. Strueder et al., "Fast Timing on Xeus," Proceedings vol. 5165, SPIE (2004), pp. 19-25.

Papp et al., A maximum information utilization approach in X-ray fluorescence analysis, Spectrochimica Acta Part B, 64, 761-770, 2009.

* cited by examiner

DYNAMIC SHAPING TIME MODIFICATION IN X-RAY DETECTORS

The present application claims priority from U.S. Provisional Patent Application Ser. No. 61/111,252, filed Nov. 4, 2008, and incorporated herein by reference.

TECHNICAL FIELD

The present invention relates to methods and apparatus for setting and modifying detector circuit parameters in real time based on energy resolution requirements, and, more particularly, to setting and modifying detector circuit parameters in response to measurements in progress.

BACKGROUND ART

The present invention is applicable to a broad class of radiation detectors in which the energy of a detected particle (typically, an x-ray photon, in the context described below) is inferred from the charge collected during the duration of a detector pulse. The number of electrons produced in a photomultiplier that detects scintillation emission in an x-ray scintillation detector is but one example relating to the class of detectors to which the present invention may be advantageously applied. In this class of detectors, the area under a plot of the pulse amplitude as a function of time is used to determine the energy of the detected particle. In such radiation detectors, it is important that the pulses be treated separately and distinctly, for purposes of inferring the integrated area under the respective pulses. If subsequent pulses pile up on top of the tails of preceding pulses, the residual amplitude of the preceding pulse tails will be imputed to the integrated areas of successive pulses.

Therefore, it has long been the practice, in the application of energy-resolving detectors, to "shape" detector pulses by shortening the pulse tails while preserving the integrated area of the pulse. This is typically accomplished by operation of a pulse processor, which will typically include a digital signal processor (DSP) executing stored software instructions. The output of the pulse processor is influenced by the values of various pulse processing parameters employed for calculation, the values of which may be prestored in the memory of or associated with the DSP. One such pulse processing parameter is the pulse shaping time. A discussion of the selection of pulse shaping time and other pulse processing parameters is set forth in Knoll, *Radiation and Detection*, 3$^{rd}$ Edition, John Wiley and Sons (2000), the disclosure of which is incorporated herein by reference.

The energy spectrum of x-rays fluoresced from a sample has been used for decades to determine its elemental and chemical composition. Applications for x-ray fluorescence (XRF) techniques are extremely wide-ranging, and include, for example, sorting alloys, analyzing soil, determining the lead concentration in painted walls, measuring quantities of toxic elements in consumer goods, and determining the thickness and composition of electroplatings. Hand-held XRF instruments, such as the Thermo Scientific Niton XRF instruments, are often purchased for multiple uses. Yet, for each specific application there is generally an optimum x-ray energy spectrum that most effectively fluoresces the sample. It is standard practice to create the optimum spectrum by changing maximum energy and filtration of the excitation beam that is incident on a sample. The source of x-ray emission may be an x-ray tube, or other x-ray source such as a radioactive source. Metal alloys, for example, are analyzed with quite different x-ray spectrum parameters than are used for studying soil. And a single test of an alloy or a soil may involve consecutive, pre-programmed changes of the high voltage and/or the filtration so as to most effectively analyze a wide range of elements in the sample. It is also standard practice to automatically adjust the intensity of the x-ray beam to maximize the number of x-rays collected during a given test time.

Co-pending U.S. patent application Ser. No. 12/426,022, to Dugas, entitled "Automated X-Ray Fluorescence Analysis" (the Application of Dugas), the entire disclosure of which is incorporated herein by reference, describes how the selection of the optimum shape of the x-ray energy spectrum incident on the target can be automated so that the user does not need prior knowledge of the type of sample being measured. However, the Dugas method does not address the spectrum of x-rays detected from the target.

Co-pending U.S. patent application Ser. No. 12/142,737, to Camus et al., incorporated herein by reference, discusses implications of multiple detection events within the course of a detector shaping time. It does not address dynamic variation of shaping times in response to resolution requirements.

SUMMARY OF THE INVENTION

In accordance with embodiments of the present invention, a method is provided for analyzing elemental composition of a sample. The method has steps of:
  a. irradiating the sample with x-rays;
  b. detecting x-rays fluoresced by the sample in response to irradiation, thereby generating detector signal pulses;
  c. preamplifying the detector signal pulses;
  d. processing the detector signal pulses subject to pulse processing parameters;
  e. determining energy resolution requirements based on analysis of sample composition; and
  f. setting at least one of the pulse processing parameters on the basis of energy resolution requirements.

In accordance with further embodiments of the invention, the pulse processing parameters may include a detector shaping time.

In accordance with another aspect of the present invention, an x-ray fluorescence instrument is provided for analyzing elemental composition of a sample. The x-ray fluorescence instrument has a source of x-rays for irradiating the sample and a detector for detecting x-rays fluoresced by the sample in response to irradiation, thereby generating detector signal pulses. The instrument also has a preamplifier for amplifying the detector signal pulses, and a signal processor for processing the detector signal pulses, as well as a controller for governing processing parameters. Finally, a signal path is provided between the controller and at least one of the signal processor and the preamplifier for varying a pulse processing parameter in accordance with composition of the sample.

In yet further embodiments of the invention, the signal processor may include a digital signal processor, the source of x-rays may be an x-ray tube. The pulse processing parameter may be a pulse shaping time.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
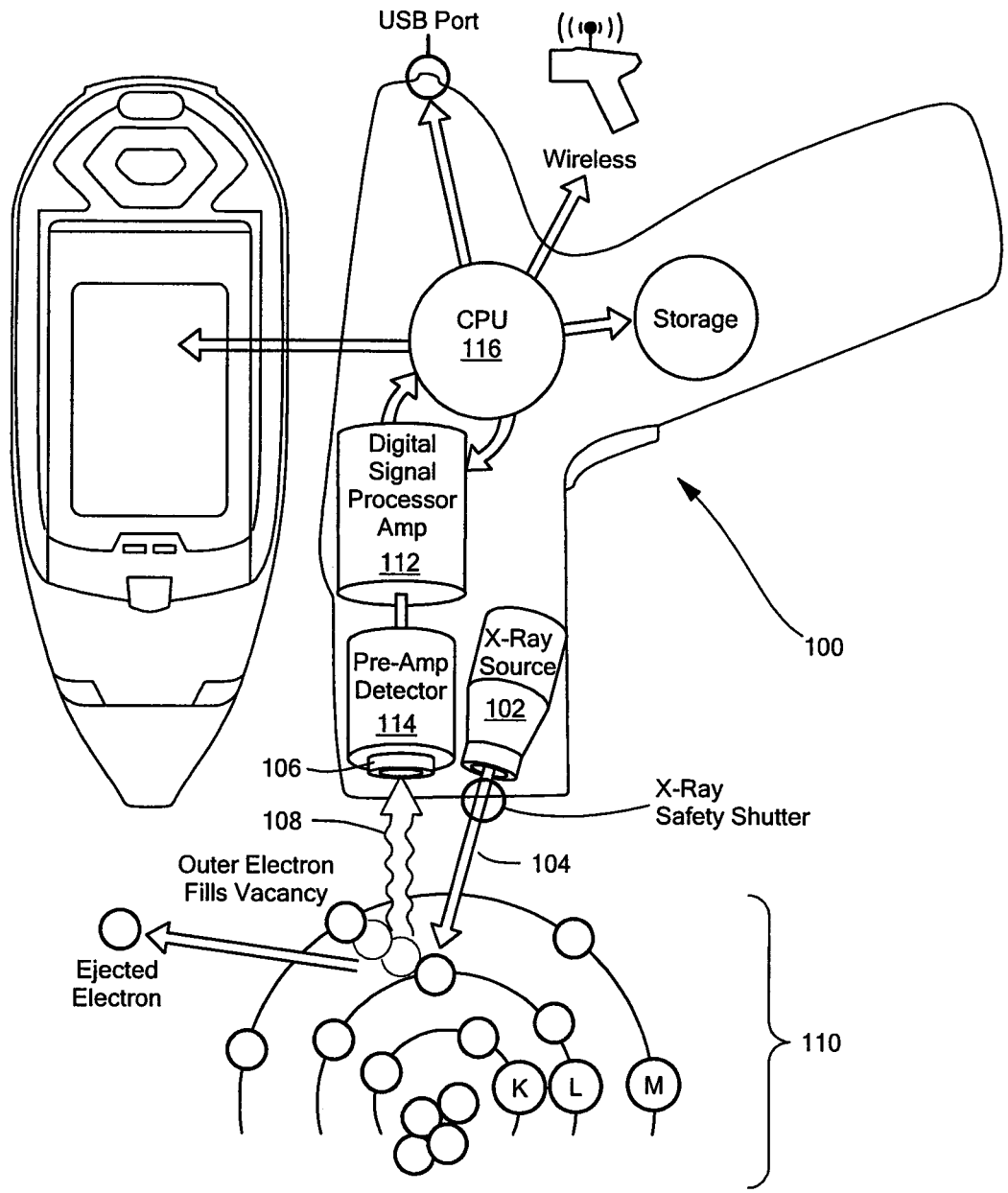
FIG. 1 is schematic depiction of an XRF instrument of a sort to which the present invention may advantageously be applied.

Portable XRF instruments, such as the Thermo Scientific line of Niton XRF detectors, are used in a wide variety of applications that require the measurement of the elemental composition of materials that can contain elements spanning most of the periodic table. X-ray spectra fluoresced from different target materials vary in complexity and intensity. Some applications require the best possible energy resolution for proper analysis while other applications can tolerate moderate energy resolution but require the shortest measurement time, i.e., the highest count rates.

In accordance with preferred embodiments of the present invention, the parameters of the pulse processor of the fluoresced signals may advantageously be changed, preferably during the course of a measurement, thereby optimizing the analysis for each application with respect to the tradeoff of energy resolution and count rate. Pulse processor parameters, otherwise referred to as detector parameters, include, without limitation, any parameter that contributes to the shape, in time, of the signal output, in response to detected radiation, of the pulse processor. Such parameters may include a shaping time or an effective decay time, but may also include more complex filtering parameters, for example, and may be implemented within the detector circuitry, to include a preamplifier and a pulse processor.

Embodiments of this invention take advantage of the strong dependence of both the detector's energy resolution and the detector's maximum count rate on the shaping time of the signals. The minimum energy resolution is reached at long shaping times, while the maximum count rates are reached at short shaping times.

As used herein, the term "energy resolution" will refer to a measure of attainable resolution, such as the full width at half maximum (FWHM) of an instrument-limited spectral feature, or the separation of two features required to satisfy the "Sparrow criterion" (that two features are sufficiently separated that a saddle, of zero first and second derivatives, appears between the two features). Either of the foregoing energy resolution criteria may serve as an example, but it is to be understood that, as used herein, a smaller energy resolution is better, for purposes of distinguishing lines. In the X-ray fluorescence spectroscopy art, the FWHM at 5.9 keV (the $K_\alpha$ line of manganese) is conventionally accepted as the measure of the resolution of the detector, and is used, accordingly, in the present description.

Pulse shaping times are typically controlled by software algorithms. The pulse shaping times can be preprogrammed for each application and each type of material the user may encounter. If an unknown sample is being analyzed, the real-time analysis of data acquired early in the analysis cycle may be used to determine the optimum pulse shaping time for the later data used in the analysis. The methods of the present invention are described, without limitation, in the context of hand-held XRF instruments that use a silicon drift detector, however it is to be understood that the scope of the invention encompasses its use in many other types of pulse counting instruments.

Preferred methods are described, with reference to FIG. 1, and without loss of generality, with reference to a hand-held XRF instrument designated generally by numeral 100. XRF instrument 100 has an x-ray tube source 102 of fluorescing radiation 104 and a silicon drift detector diode (SDD) or other detector 106 to detect the fluoresced x-rays 108. An elemental atom giving rise to fluoresced x-rays 108 is depicted schematically as numeral 110. The SDD is a preferred detector for application of the present invention because its throughput can vary from twenty-five thousand signals per second for long pulse-shaping times to more than a hundred thousand signals per second for short pulse-shaping times. The cost of shortening pulse shaping times and thereby increasing the number of detections per second is the degradation of detector spectral resolution. That trade is quantitatively justified for a number of applications. The inverse trade is also justified for some applications where the signal to noise ratio obtained from an improved detector resolution more than offsets the loss in signal strength due to a lower peak counting rate.

The minimum concentration of an element that can be detected in a given time is determined in large part by the strength of the signal from that element and by the ratio of the signal to the noise under the signal. Embodiments of the present invention make use of the fact that these two quantities are not only functions of the fluorescing x-ray spectrum, as described in the aforementioned Application of Dugas, but are also functions of electronically adjustable parameters that modify and control the detected signals.

In accordance with preferred embodiments of the present invention, parameters of a digital signal processor (DSP) 112 (shown in FIG. 1) are changed, and, in particular, the pulse shaping time, where the DSP parameters, together, at least partially determine the detector resolution and the detector count rate so as to obtain the most accurate analysis of a sample in a given test time. The optimum pulse shaping parameters may be preprogrammed for each type of sample that the XRF instrument is expected to test. When the sample type is unknown, or the operator is inspecting a mixture of sample types, the optimum pulse shaping parameters can be determined from the data collected during the first seconds of a test using the analytic methods described in the Dugas Application. It is to be understood that, while pulse shaping times are determined, in a preferred embodiment, by parameters of the DSP 112, it is to be understood that modification of pulse shaping times or other pulse shaping parameters may be achieved otherwise, within the scope of the present invention, such as by programming values of circuit components within a detector preamplifier 114, or otherwise. It is also to be understood that pulse shaping parameters are not limited to RC times, and, indeed, time constants applied on the rising and falling edges of pulses need not be identical, and higher order effective filters may also be applied to shape pulses, in accordance with the scope of the present invention.

In accordance with embodiments of the present invention, pulse shaping times of the detected pulses may be modified based on the type of samples under test, and may also be changed, during the course of measurement, on the basis of on-line analysis of data accumulated up to that change. Adjustment of pulse shaping is typically performed in addition to the adjustments of the shape of the incoming fluorescing x-ray beam. When the operator knows the sample type, the sample type may be selected from a list of options presented on the menu screen so that the pre-programmed changes to the x-ray spectrum and pulse shape are implemented. When the sample is not known, or when a variety of samples need to be rapidly tested and sorted, the accumulated spectrum is used to automatically select the appropriate parameters to obtain the most accurate results.

While it is preferable that a semiconductor detector be operated at such a cold temperature as to render thermal noise negligible, that ideal is not yet practical for hand-held XRF instruments. Portable XRF instruments may use thermoelectric Peltier coolers to cool the detector and first preamp components. However, the advantageous size, weight and ease of programming of Peltier coolers are offset by their poor efficiency of the cooler.

Returning, now, to FIG. 1, X-ray source 102 is preferably an x-ray tube, and detector 106 is preferably an SDD, though other sources and detectors may be substituted within the scope of the claimed invention. X-ray tube 102 operates at a tube voltage HV and with an electron beam current I, and generates an x-ray beam 104 that passes through a filter before impinging on a target represented schematically by elemental atom 110. The fluoresced x-rays 108 are detected in the SDD 106. Individual signals from the detector are sorted according to the electric charge they deposit in the SDD. Characteristic lines of the detected elements have a Gaussian shape specified by a mean energy and a full width at half the maximum height (FWHM). The FWHM at 5.9 keV is universally accepted as the measure of the resolution of the detector itself. The detector resolution at lower and higher energies can be calculated from the measurement of the resolution at 5.9 keV (the $K_\alpha$ line of manganese) together with the knowledge of the intrinsic resolution of the particular type of detector. The noise-free (intrinsic) resolution of an SDD detector is approximately 110 eV. This is the resolution due only to the statistical variation of the number of electrons and holes collected from the detection of a 5.9 keV x-ray. The actual resolution is determined by the sum, in quadrature, of the intrinsic resolution and the noise contributions at 5.9 keV.

Figure 2:
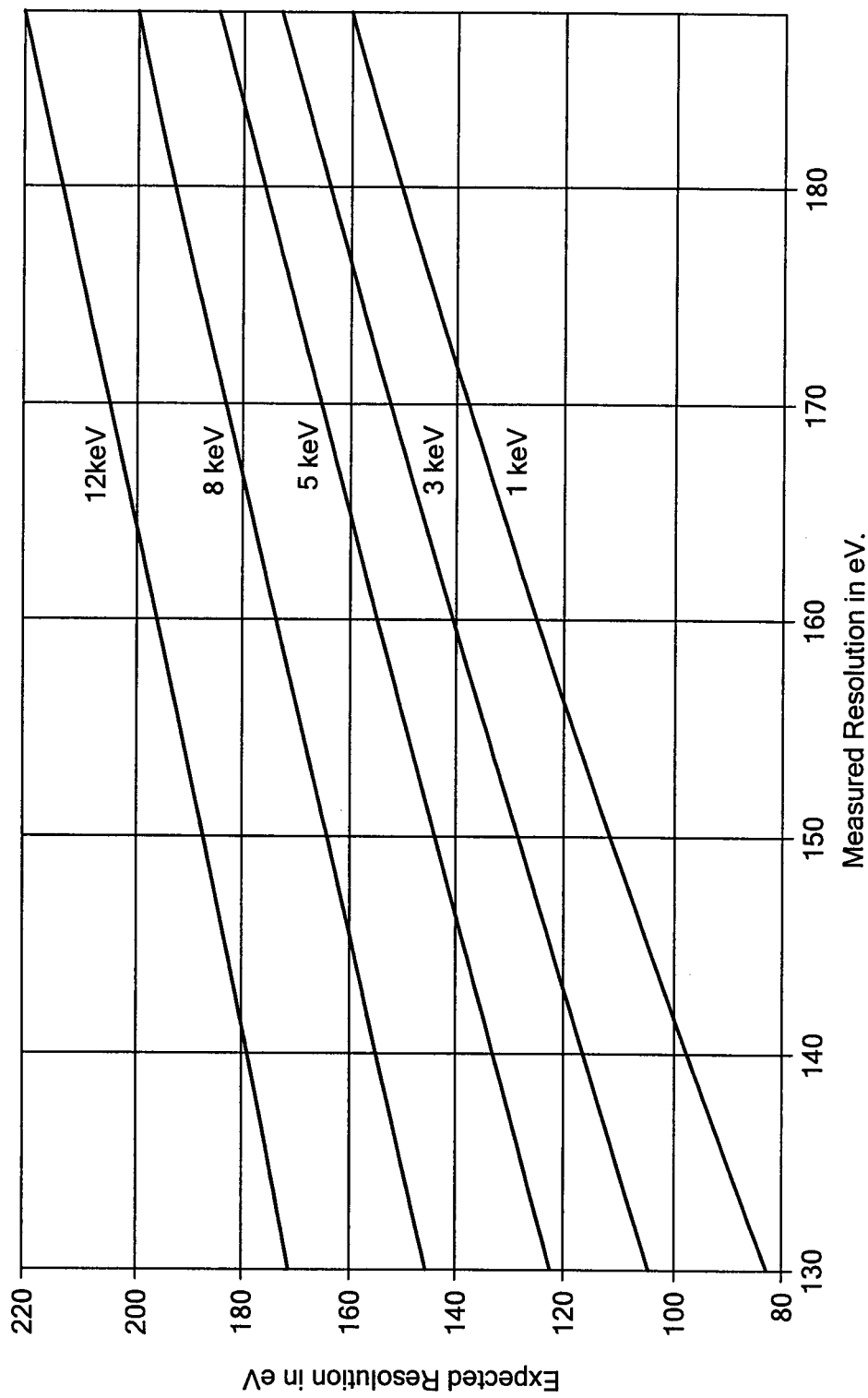
FIG. 2 shows plots of the expected resolution of a silicon drift detector diode as a function of energies varying from 1 keV to 12 keV, plotted as a function of measured resolution at 5.9 keV.

FIG. 2 shows the expected resolution of an SDD for x-rays at energies varying from 1 keV to 12 keV, as a function of the measured resolution at 5.9 keV. Two aspects are noteworthy in the present context:

First, the graphs plotted in FIG. 2 illustrate that the resolution of low-energy x-rays (referring, here, to x-rays at energies 3 keV or below) is improved significantly by improving the resolution at 5.9 keV. For example, if the SDD has a resolution of 180 eV at 5.9 keV, the resolution at 1 keV (the $K_\alpha$ line of magnesium) is expected to be about 150 eV, an improvement of 17%. If, however, the SDD can attain a resolution of 155 eV, the resolution at 1 keV will improve to 120 eV, an improvement of 33%. It should be noted that improved resolution is especially important in the low energy region of the x-ray spectrum, which is often crowded with characteristic K x-ray lines of light elements, L lines from medium weight elements, and M lines from heavy elements. Thus, when the low energy region is a spectral region of interest, longer shaping times, and thus greater spectral resolution, is set by the controller 116.

Second, FIG. 2 shows that the widths of all peaks in a spectrum are narrowed or broadened together when the detector resolution at 5.9 keV is diminished or enlarged, respectively. Those changes must be taken into account in the analysis program that produces the quantitative results of elemental concentrations, and, while the accounting is non-trivial, may be done rapidly since the energy resolution of a characteristic x-ray is a pre-determined function of its energy.

Figure 3:
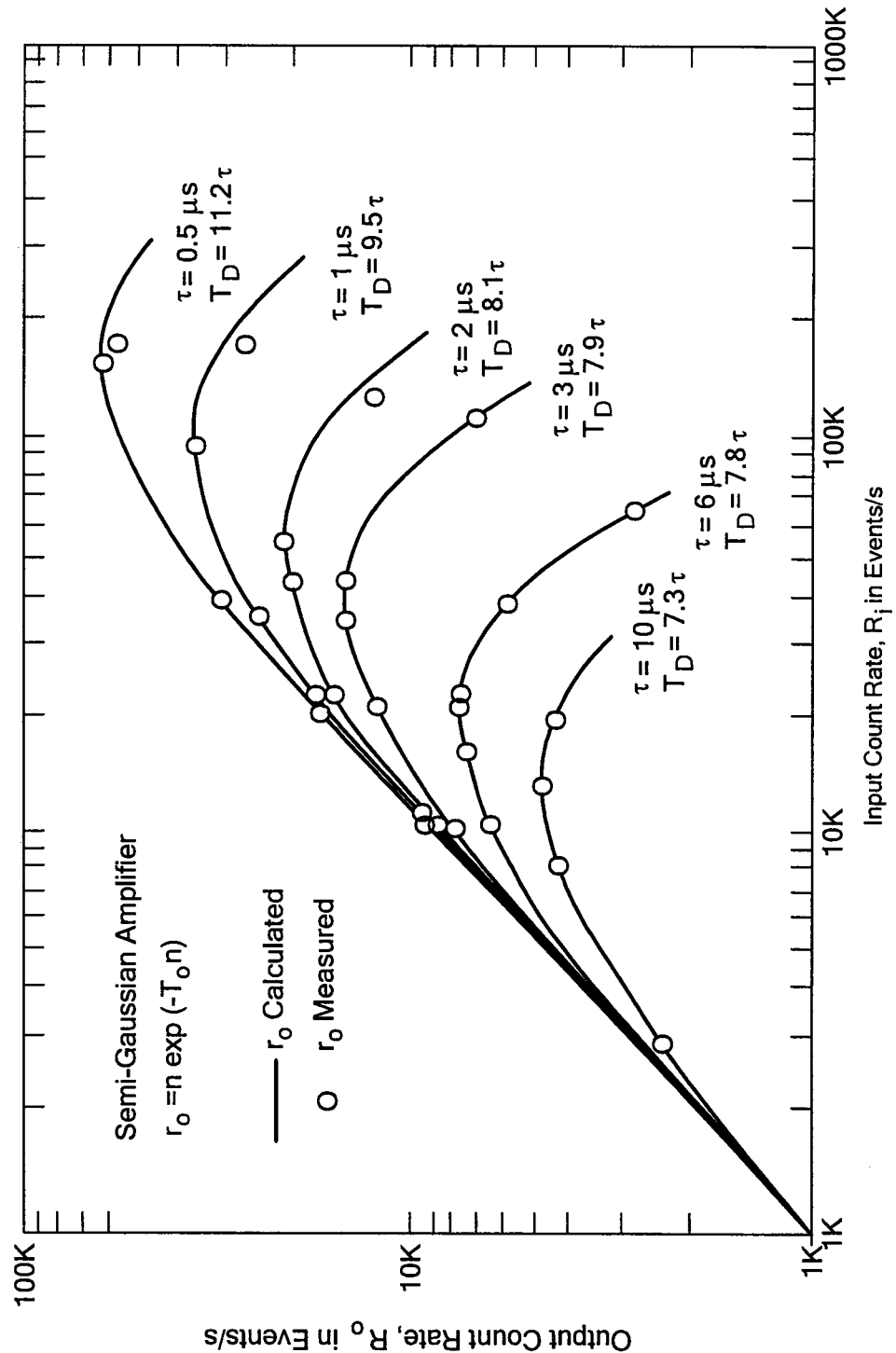
FIG. 3, reproduced from an on-line tutorial by Ortec, shows an empirical relationship between the throughput count rate, plotted logarithmically on the ordinate, and the pulse shaping time, indicated beneath each of the respective curves.

FIG. 3, reproduced from an on-line tutorial by Ortec, shows an empirical relationship between the throughput count rate, plotted logarithmically on the ordinate, and the pulse shaping time, indicated beneath each of the respective curves. The count rate out of a pulse amplifier is plotted as a function of the count rate of pulses into an amplifier, for shaping times ranging from 0.5 µs to 10 µs. The graphs are specific to a germanium detector and not to an SDD but well illustrate the point that the electronically created shape of the pulse determines the maximum analyzable count rate. When the shaping time is 10 µs, the maximum throughput is only about 5,000 counts per second, attained at an input count rate of about 10,000 counts per second. When the shaping time is reduced to 1 µs, the throughput as increased to 50,000 counts per second.

The present invention has been implemented using an SDD detector with the following specifications: At a pulse shaping time of 4 µs, the maximum throughput is about 50,000 counts per second and the detector resolution is 155 eV. When the pulse shaping time was reduced to 1 µs, the maximum rate rose to 160,000 counts per second and the detector resolution worsened to 175 eV as a result of the increase in the noise level with decreasing shaping time. Reducing the shaping time increased the counts in each characteristic line by a factor of 4. The ratio of the signal to the noise of isolated higher-energy peaks remained almost unchanged so the minimum level of detection of elements improved by almost a factor of two.

Figure 4:
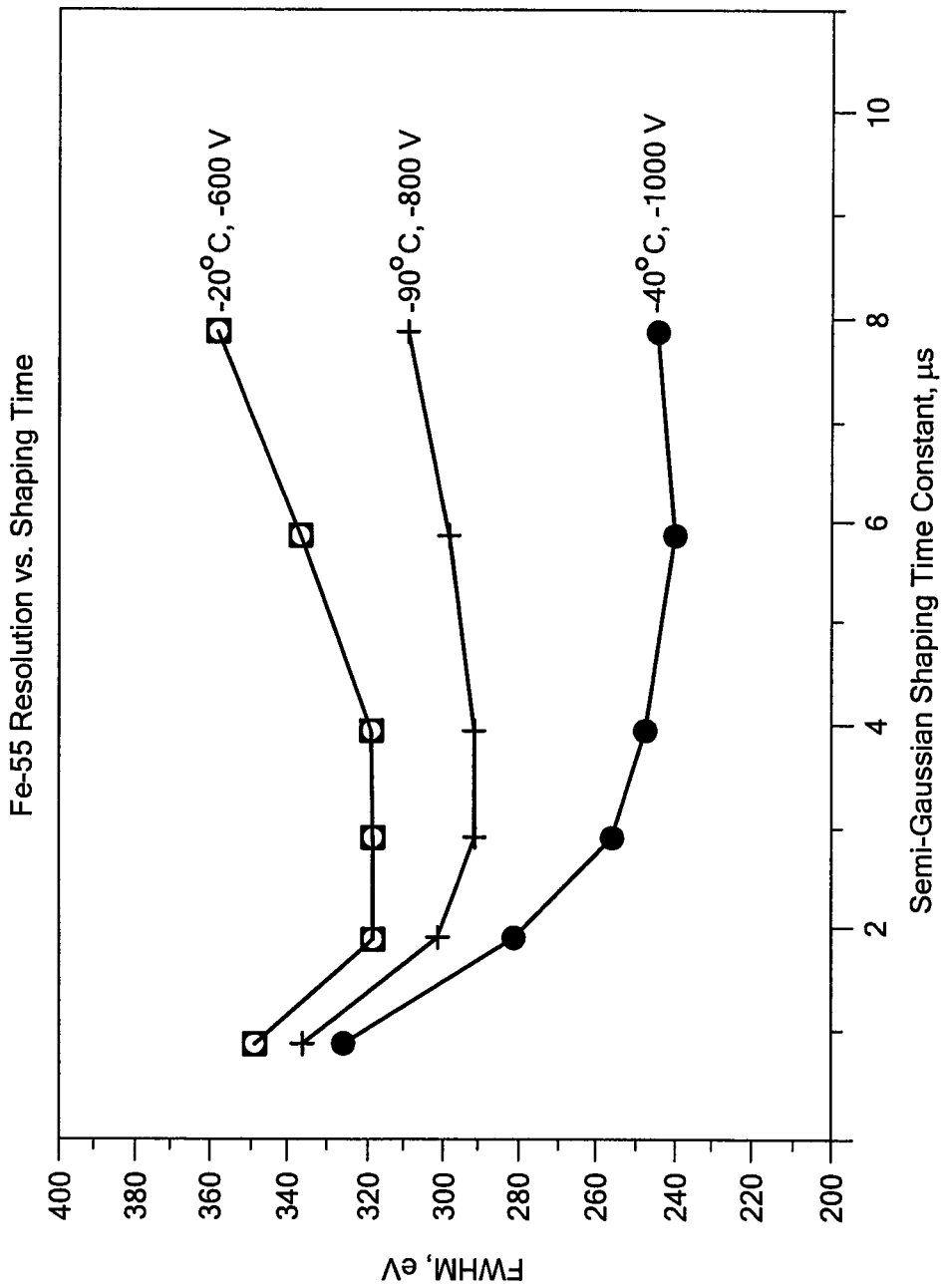
FIG. 4 plots the effect of the shaping time and the detector temperature on the resolution of a CdZnTe semiconductor detector.

FIG. 4, reproduced from Niemela et al., *Evaluation of CdZnTe detectors for soft X-Ray applications*, IEEE Transactions on Nuclear Science, vol. 41, pp. 1054-57 (1994), incorporated herein by reference, shows the effect of the shaping time and the detector temperature on the resolution of a CdZnTe semiconductor detector of x-rays. While the data for an SDD detector differ from that of FIG. 4, the general phenomena will be the same. When the detector temperature is so low that thermal noise is inconsequential (the −40° C. curve in FIG. 3) the resolution of the 5.9 keV x-ray improves as the shaping time increases, reaching minimum of 250 eV at a shaping time of about 6 µs. As the temperature of the detector is raised, the best resolution worsens; it is 290 eV at −30° C. and 320 eV at 20° C. For our SDD detector operating at −35° C., the resolution is ~175 eV at a shaping time of 1 µs, and 160 eV at a shaping time of 4 µs. Cooling the detector to −45° C. lowers both the resolution times by about 10 eV.

Figure 5:
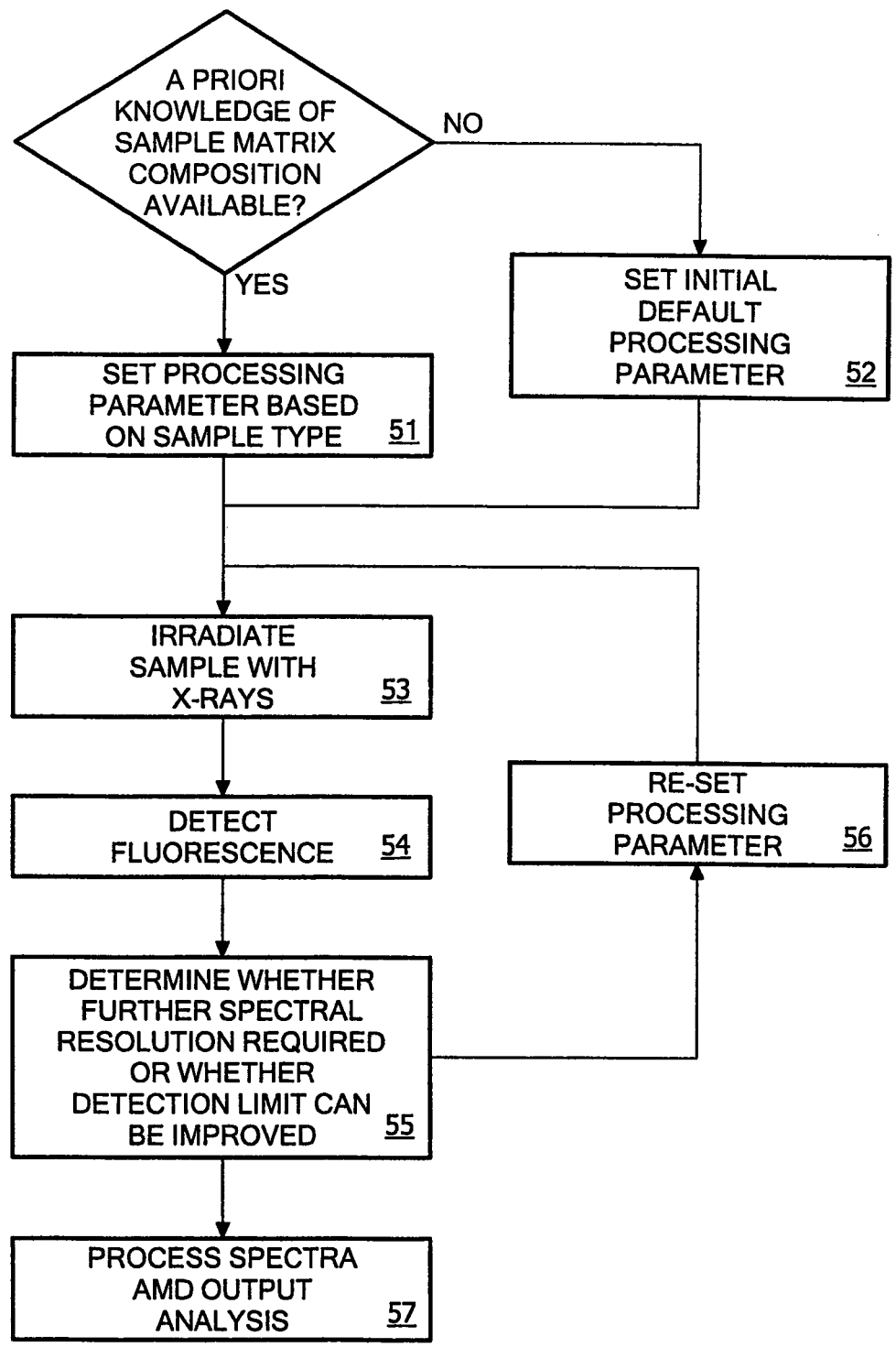
FIG. 5 is a flowchart depicting dynamic modification of the shaping time of detector electronics in accordance with an embodiment of the present invention.

Embodiments of the present invention provide improved performance of XRF analyzers by optimizing the pulse shaping time for a particular sample. Referring now to the flowchart of FIG. 5, when a priori knowledge of the sample matrix is available, the operator may select a sample type (e.g., via a touch-screen interface) from a list of candidate sample types, and the sample is then analyzed in accordance with one or more pre-stored processing parameters, such as pulse shaping time information corresponding to the selected sample type, as indicated in step 51. In instances where a priori knowledge of the sample is not available, then the pulse shaping time, initially set to a default value (step 52) may be adaptively adjusted during an analysis cycle based on data acquired and processed early in the analysis cycle. More specifically, the sample is irradiated with a beam of x-rays generated, for example, by x-ray source 102 of FIG. 1 to cause the emission of characteristic fluoresced x-rays by atoms in the sample, step 53. The detector receives the fluoresced x-rays and responsively produces pulses representative of the energies and intensities of the x-rays, step 54. The pulses produced by the detector are shaped in accordance with the pulse processing parameters set in steps 51 or 52. The processed pulses are conveyed to the controller, which analyzes the accumulated pulses to create an energy spectrum of the detected x-rays. This analysis of the processed pulses and generation of the energy spectrum occurs in real-time, i.e., substantially concurrently with the irradiation/detection steps. As the energy spectral data are accumulated, the controller analyzes the data to determine whether components of the spectrum meets targeted performance criteria, for example energy resolution or count rate, step 55. If the controller determines that the targeted performance criteria are not satisfied, then the pulse processing parameter(s) is or are adjusted so as to achieve satisfactory performance; for example, the pulse shaping time applied to the detector pulses may be increased to improve energy resolution, step 56. The analysis cycle, consisting of irradiation, detection and spectrum acquisition, is then continued at the adjusted pulse processing parameters, step 57, in accordance with stored instructions. It should be noted that the changed energy resolution of the detector arising from the adjusted pulse processing parameter(s), and the energy calibration of the detector, must be factored into the real-time analysis of the data. The adjustment algorithm is programmed into the DSP since, for a given model of detector, the energy resolution and energy calibration of a pulse processing system is a fixed function of the pulse processing parameters. The analysis cycle will typically terminate after a specified time period or when certain spectrum characteristics (e.g., signal-to-noise ratios) have been achieved or when the statistical uncertainties of the elemental concentrations have reached a predetermined level.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for analyzing elemental composition of a sample, the method comprising:
 a. irradiating the sample with x-rays;
 b. detecting x-rays fluoresced by the sample in response to irradiation, thereby generating detector signal pulses;
 c. preamplifying the detector signal pulses;
 d. processing the detector signal pulses subject to pulse processing parameters;
 e. determining energy resolution requirements based on analysis of sample composition; and
 f. setting at least one of the pulse processing parameters on the basis of the determined energy resolution requirements.

2. A method in accordance with claim 1, wherein the at least one of the pulse processing parameters includes a detector shaping time.

3. An x-ray fluorescence instrument for analyzing elemental composition of a sample, the instrument comprising:
 a. a source of x-rays for irradiating the sample;
 b. a detector for detecting x-rays fluoresced by the sample in response to irradiation, thereby generating detector signal pulses;
 c. a preamplifier for amplifying the detector signal pulses;
 d. a signal processor for processing the detector signal pulses;
 e. a controller for governing processing parameters; and
 f. a signal path between the controller and at least one of the signal processor and the preamplifier, so that a pulse processing parameter can be varied in accordance with composition of the sample.

4. An x-ray fluorescence instrument in accordance with claim 3, wherein the signal processor includes a digital signal processor.

5. An x-ray fluorescence instrument in accordance with claim 3, wherein the source of x-rays is an x-ray tube.

6. An x-ray fluorescence instrument in accordance with claim 3, wherein the pulse processing parameter is a detector shaping time.

* * * * *